(12) United States Patent
Grode et al.

(10) Patent No.: US 8,545,854 B2
(45) Date of Patent: Oct. 1, 2013

(54) TUBERCULOSIS VACCINE WITH IMPROVED EFFICACY

(75) Inventors: Leander Grode, Berlin (DE); Stefan H. E. Kaufmann, Berlin (DE); Baerbel Raupach, Berlin (DE); Juergen Hess, Balersdorf (DE)

(73) Assignee: Max-Planck-Gesellschaft zur Foerderung der Wissenshaften, e.V., Munich (DE)

( * ) Notice: Subject to any disclaimer, the term of this patent is extended or adjusted under 35 U.S.C. 154(b) by 0 days.

(21) Appl. No.: 13/165,904

(22) Filed: Jun. 22, 2011

(65) Prior Publication Data

US 2012/0027794 A1     Feb. 2, 2012

Related U.S. Application Data

(62) Division of application No. 10/554,408, filed as application No. PCT/EP2004/004345 on Apr. 23, 2004, now Pat. No. 7,988,980.

(60) Provisional application No. 60/464,644, filed on Apr. 23, 2003.

(51) Int. Cl.
    *A61K 39/04*     (2006.01)
    *A61K 49/00*     (2006.01)
    *C07H 21/04*     (2006.01)

(52) U.S. Cl.
    USPC .......... 424/248.1; 424/9.1; 424/9.2; 435/7.1; 435/7.2; 530/300; 530/350; 536/23.1; 536/23.7

(58) Field of Classification Search
    USPC .............. 424/9.1, 9.2, 248.1; 435/7.1, 7.2; 530/300, 350; 536/23.1, 23.7
    See application file for complete search history.

(56) References Cited

U.S. PATENT DOCUMENTS 6,673,353 B1    1/2004  Kaufmann et al.
7,988,980 B2 *  8/2011  Grode et al. ............... 424/248.1

FOREIGN PATENT DOCUMENTS

WO    WO 99/10496 A    3/1999

OTHER PUBLICATIONS

Grode et al., "Increased vaccine efficacy against tuberculosis of recombinant *Mycobacterium bovis* bacille Calmette-Guerin mutants that secrete listeriolysin", The Journal of Clinical Investigation, vol. 115, No. 9, Sep. 2005, pp. 2472-2479.
Jones et al., "Characterization of *Listeria monocytogenes* Pathogenesis in a Strain Expressing Perfringolysin O in Place of Listeriolysin O", Infection and Immunity, Dec. 1994, p. 5608-5613.
Portnoy et al., Capacity of Listeriolysin O, Streptolysin O, and Perfringolysin O to Mediate Growth of *Bacillus subtilis* within Mammalian Cells, Infection and Immunity, vol. 60, No. 7, Jul. 1992, p. 2710-2717.
Rinsho to biseibutsu (Clinic and Microbes), 1997, vol. 24, No. 1, pp. 37-43.
Sambrook et al., Molecular Cloning, A laboratory Manual. Cold Spring Harbor Laboratory Press (1989), 1.101-1.104.
Sambrook & Russell, Molecular Cloning, A Laboratory Manual, 3rd edition, (2001) vol. 2, 10.47, formula (3).
Nagy et al., Effect of perfringolysin O on the lateral diffusion constant of membrane proteins of hepatocytes as revealed by fluorescence recovery after photobleaching., Biochim Biophys Acta., 1988, 939(3), 551-560.
Awad and Rood, Perfringolysin O expression in *Clostridium perfringens* is independent of the upstream pfoR gene., Journal of Bacteriology, 2002, 184(7), 2034-2038.
Hess et al., "*Mycobacterium bovis* bacille Calmette-Guérin strains secreting listeriolysin of *Lysteria monocytogenes*", Proceedings of the National Academy of Sciences of USA, vol. 95, Apr. 1, 1998, pp. 5299-5304.
Reyrat et al., "Urease activity does not contribute dramatically to persistence of *Mycobacterium bovis* bacillius Calmette-Guerin", Infection and Immunity, vol. 64, No. 9, 1996, pp. 3934-3936.
Reyrat et al., "The urease locus of *Mycobacterium tuberculosis* and its utilization for the demonstration of allelic exchange in *Mycobacterium bovis* bacillus Calmette-Guerin", Proceedings of the National Academy of Sciences of the United States of America, vol. 92, No. 19, 1995, pp. 8768-8772.
Clemens et al., "Purification characterization and genetic analysis of *Mycobacterium tuberculosis* urease, a potentially critical determinant of host-pathogen interaction", J.Bacteriology, vol. 177, No. 19, 1995, pp. 5644-5652.
Guleria et al., "Auxotrophic vaccines for tuberculosis", Nature Medicine, vol. 2, No. 3, Mar. 1996, pp. 334-337.
Kremer, L., et al. Infection and Immunity, vol. 68, No. 7, pp. 4264-4273, Jul. 2000.
Guenounou, M. Immuno-Analyse et Biologie Specialisee, vol. 12, No. 2, pp. 65-69, May 1997.
Eun-Kyeong, J. Current Opinion in Infectious Diseases, vol. 16, No. 3, pp. 205-210, 2003.
Fujiwara, R.T., et al. PLoS Neglected Tropical Diseases, vol. 3, No. 3, article e399, Mar. 2009.
Zhong, J. European Journal of Immunology, vol. 38, No. 1, pp. 73-81, Jan. 2008.

* cited by examiner

*Primary Examiner* — Rodney P. Swartz
(74) *Attorney, Agent, or Firm* — Rothwell, Figg, Ernst & Manbeck, P.C.

(57) ABSTRACT

The present invention relates to novel recombinant vaccines providing protective immunity against tuberculosis. Further, the present invention refers to novel recombinant nucleic acid molecules, vectors containing said nucleic acid molecules, cells transformed with said nucleic acid molecules and polypeptides encoded by said nucleic acid molecules.

35 Claims, 4 Drawing Sheets

TUBERCULOSIS VACCINE WITH IMPROVED EFFICACY

This application is a divisional of Ser. No. 10/554,408 filed Nov. 30, 2006, now U.S. Pat. No. 7,988,980, which is a 35 U.S.C. 371 National Phase Entry Application from PCT/EP2004/004345, filed Apr. 23, 2004, which claims the benefit of U.S. Provisional Application No. 60/464,644 filed on Apr. 23, 2003, the disclosure of which are incorporated herein by their entirety by reference.

DESCRIPTION

The present invention relates to novel recombinant vaccines providing protective immunity especially against tuberculosis.

Tuberculosis (TB) caused by *Mycobacterium tuberculosis* remains a significant global problem. It is estimated that one third of the world's population is infected with *M. tuberculosis* (Kochi, 1991). In many countries the only measure for TB control has been vaccination with *M. bovis* bacille Calmette-Guérin (BCG). The overall vaccine efficacy of BCG against TB, however, is about 50% with extreme variations ranging from 0% to 80% between different field trials (Roche et al., 1995). Thus, BCG should be improved, e.g. by genetic engineering, to provide a vaccine for better TB control (Murray et al., 1996; Hess and Kaufmann, 1993). The widespread emergence of multiple drug-resistant *M. tuberculosis* strains additionally underlines the urgent requirement for novel TB vaccines (Grange, 1996).

*M. tuberculosis* belongs to the group of intracellular bacteria that replicate within the phagosomal vacuoles of resting macrophages, thus protection against TB depends on T cell-mediated immunity (Kaufmann, 1993). Several studies in mice and humans, however, have shown that Mycobacteria stimulate antigen-specific, major histocompatibility complex (MHC) class II- or class I-restricted CD4 and CD8 T cells, respectively (Kaufmann, 1993).

The important role of MHC class I-restricted CD8 T cells was convincingly demonstrated by the failure of β2-microglobulin (β2m) deficient mice to control experimental *M. tuberculosis* infection (Flynn et al., 1993). Because these mutant mice lack MHC class I, functional CD8 T cells cannot develop. In contrast to *M. tuberculosis* infection, β2m-deficient mice are capable of controlling certain infectious doses of the BCG vaccine strain (Flynn et al., 1993; Ladel et al., 1995). Furthermore, BCG vaccination of β2m-deficient mice prolonged survival after subsequent *M. tuberculosis* infection whereas BCG-immunized C57BL/6 resisted TB (Flynn et al., 1993). This differential CD8 T cell dependency between *M. tuberculosis* and BCG may be explained as follows: *M. tuberculosis* antigens gain better access to the cytoplasm than antigens from BCG leading to more pronounced MHC class I presentation (Hess and Kaufmann, 1993). Consequently, a more effective CD8 T cell response is generated by *M. tuberculosis*. This notion was recently supported by increased MHC class I presentation of an irrelevant antigen, ovalbumin, by simultaneous *M. tuberculosis*, rather than BCG, infection of antigen presenting cells (APC) (Mazzaccaro et al., 1996).

Secreted proteins of *M. tuberculosis* comprise a valuable source of antigens for MHC class I presentation. Recently, a DNA vaccine encoding the secreted antigen Ag85A elicited MHC class I-restricted CD8 T cell responses in mice which may contribute to defence against TB (Huygen et al., 1996). In general, evidence is accumulating that immunization with secreted protein antigens of *M. tuberculosis* induce some protection against TB in guinea pigs and mice (Horwitz et al., 1995; Andersen, 1994). An important goal towards the development of improved TB vaccines based on BCG, therefore, is to augment the accessibility of secreted BCG-specific antigens to the cytoplasm of infected APC. Subsequent delivery of peptides derived from these secreted proteins into the MHC class I presentation pathway may potentiate the already existing BCG-specific immune response for preventing TB.

The phagolysosomal escape of *L. monocytogenes* represents a unique mechanism to facilitate MHC class I antigen presentation of listerial antigens (Berche et al., 1987; Portnoy et al., 1988). Listeriolysin (Hly), a pore-forming sulfhydryl-activated cytolysin, is essential for the release of *L. monocytogenes* microorganisms from phagolysosomal vacuoles into the cytosol of host cells (Gaillard at al., 1987; Portnoy et al., 1988). This escape function was recently transferred to *Bacillus subtilis* and to attenuated *Salmonella* ssp. strains (Bielecki et al., 1991; Gentschev et al., 1995; Hess and Kaufmann, 1997). Hly expression by an asporogenic *B. subtilis* mutant strain or in *Salmonella* ssp. results in bacterial escape from the phagolysosome into the cytosol of J774 macrophage-like cells (Bielecki et al., 1991; Gentschev et al., 1995; Hess and Kaufmann, 1997).

WO 99/101496 and Hess et al. (1998) disclose recombinant *Mycobacterium bovis* strains that secrete biologically active Listeriolysin fusion proteins. These *M. bovis* strains have been shown to be effective vaccines against TB in several animal models.

According to the present invention Hly was expressed in urease-deficient BCG strains. These urease-deficient BCG strains exhibit an increased Hly activity in phagosomes and in turn improved pore formation in the endosomal membranes leading to superior immunoprotectivity. Further, urease-deficient BCG-Hly strains are involved in apoptotic processes which may contribute to an enhanced immune protection. Thus, the urease-deficient BCG strains have an even further improved vaccine capacity. Further, it was surprisingly found that urease-deficient BCG strains exhibit an increased safety profile compared to BCG parent strains and thus are particularly suitable for the vaccination of immunodeficient patients.

A first aspect of the present invention is a bacterial cell, particularly a *Mycobacterium* cell which is urease-deficient and comprises a recombinant nucleic acid molecule encoding a fusion polypeptide comprising (a) at least one domain from a polypeptide, wherein said polypeptide domain is capable of eliciting an immune response in a mammal, and (b) a phagolysosomal escape domain. It is preferred that the cell is capable of expressing the nucleic acid molecule of the invention. More preferably, the cell is capable of secreting the fusion polypeptide and/or of providing it in a form suitable for MHC class I-restricted antigen recognition.

The bacterial cell of the invention is a urease-deficient cell, e.g. a gram-negative or a gram-positive bacterial cell, preferably a *Mycobacterium* cell. The urease-deficiency may be achieved by partially or completely inactivating one or several cellular nucleic acid molecules which code for a urease subunit, particularly ureA encoding for urease subunit A, ureB coding for urease subunit B and/or ureC coding for urease subunit C. The sequences of ureA, ureB and ureC in Mycobacteria, particularly *M. bovis* and *M. tuberculosis* and the proteins encoded thereby are described by Reyrat et al. (1995) and Clemens et al. (1995), which are incorporated herein by reference.

Preferably the urease-deficient bacterial strain is obtained by deletions and/or insertions of one or several nucleotides in urease subunit—coding nucleic acid sequences and/or their expression control sequences. Deletions and/or insertions may be generated by homologous recombination, transposon insertion or other suitable methods.

In an especially preferred embodiment the ureC sequence is inactivated, e.g. by constructing a suicide vector containing a ureC gene disrupted by a selection marker gene, transforming the target cell with the vector and screening for selection marker-positive cells having a urease negative phenotype as described by Reyrat et al. (1995).

The cell of the invention is preferably an M. bovis cell, a M. tuberculosis cell, particularly an attenuated M. tuberculosis cell or other Mycobacteria, e.g. M. microti, M. smegmatis, M. canettii, M. marinum or M. fortuitum or Mycobacteria as described by Reyrat et al. (1995).

The Mycobacterium cell of the invention comprises a recombinant nucleic acid molecule, e.g. the nucleic acid molecule in SEQ ID No.1. This nucleic acid molecule comprises a signal peptide coding sequence (nucleotide 1-120), a sequence coding for an immunogenic domain (nucleotide 121-153), a peptide linker coding sequence (nucleotide 154-210), a sequence coding for a phagolysosomal domain (nucleotide 211-1722), a further peptide linker coding sequence (nucleotide 1723-1800) and a sequence coding for a random peptide (nucleotide 1801-1870). The corresponding amino acid sequence is shown in SEQ ID No.2.

The nucleic acid contains at least one immunogenic domain from a polypeptide. The immunogenic domain may be derived from an organism of the genus Mycobacterium, preferably from Mycobacterium tuberculosis or from Mycobacterium bovis. This domain has a length of at least 6, preferably of at least 8 amino acids. The immunogenic domain is preferably a portion of a native Mycobacterium polypeptide. However, within the scope of the present invention is also a modified immunogenic domain, which is derived from a native immunogenic domain by substituting, deleting and/or adding one or several amino acids.

The immunogenic domain is however not restricted to Mycobacterium antigens and can be selected from autoantigens, tumor antigens and pathogen antigens such as virus antigens, parasite antigens, bacterial antigens in general and immunogenic fragments thereof. Specific examples for suitable tumor antigens are human tumor antigens such as the p53 tumor suppressor gene product (Houbiers et al., 1993) and melanocyte differentiation antigens, e.g. Melan-A/MART-1 and gp100 (van Elsas at al., 1996). Specific examples for suitable virus antigens are human tumor virus antigens such as human papilloma virus antigens, e.g. antigens E6 and E7 (Bosch et al., 1991), influenza virus antigens, e.g. influenza virus nucleoprotein (Matsui et al., 1995; Fu et al., 1997) or retroviral antigens such as HIV antigens, e.g. the HIV-1 antigens p17, p24, RT and Env (Harrer et al., 1996; Haas et al., 1996). Specific examples for suitable parasite antigens are Plasmodium antigens such as liver stage antigen (LSA-1), circumsporozoite protein (CS or allelic variants cp26 or cp29), thrombospondin related amonymous protein (TRAP), sporozoite threonine and asparagine rich protein (STARP) from Plasmodium falciparum (Aidoo et al., 1995) and Toxoplasma antigens such as p30 from Toxoplasma gondii (Khan et al., 1991; Bulow and Boothroyd, 1991). Specific examples for suitable bacterial antigens are Legionella antigens such as Major secretory protein from Legionella pneumophila (Blander and Horwitz, 1991).

The immunogenic domain is capable of eliciting an immune response in a mammal. This immune response can be a B cell-mediated immune response. Preferably, however, the immunogenic domain is capable of eliciting a T cell-mediated immune response, more preferably a MHC class I-restricted CD8 T cell response.

The domain capable of eliciting an immune response is more preferably selected from immunogenic peptides or polypeptides from M. bovis or M. tuberculosis or from immunogenic fragments thereof. Specific examples for suitable antigens are Ag85B (p30) from M. tuberculosis (Harth et al., 1996), Ag85B (α-antigen) from M. bovis BCG (Matsuo et al., 1988), Ag85A from M. tuberculosis (Huygen et al., 1996) and ESAT-6 from M. tuberculosis (Sorensen et al., 1996, Harboe et al., 1996 and Andersen at al., 1995). More preferably, the immunogenic domain is derived from the antigen Ag85B. Most preferably, the immunogenic domain comprises the sequence from aa.41 to aa.51 in SEQ ID No.2.

The recombinant nucleic acid molecule according to the present invention further comprises a phagolysosomal escape domain, i.e. a polypeptide domain which provides for an escape of the fusion polypeptide from the phagolysosome into the cytosol of mammalian cells. Preferably, the phagolysosomal escape domain is a Listeria phagolysosomal escape domain, which is described in U.S. Pat. No. 5,733,151, herein incorporated by reference. More preferably, the phagolysosomal escape domain is derived from the organism L. monocytogenes. Most preferably, the phagolysosomal domain is encoded by a nucleic acid molecule selected from: (a) a nucleotide sequence comprising nucleotides 211-1722 as shown in SEQ ID No.1, (b) a nucleotide sequence which encodes for the same amino acid sequence as the sequence from (a), and (c) a nucleotide sequence hybridizing under stringent conditions with the sequence from (a) or (b).

Apart from the nucleotide sequence depicted in SEQ ID No.1 the present invention also comprises nucleic acid sequences hybridizing therewith. In the present invention the term "hybridization" is used as defined in Sambrook et al. (Molecular Cloning. A laboratory manual, Cold Spring Harbor Laboratory Press (1989), 1.101-1.104). In accordance with the present invention the term "hybridization" is used if a positive hybridization signal can still be observed after washing for one hour with 1×SSC and 0.1% SDS at 55° C., preferably at 62° C. and more preferably at 68° C., particularly for 1 hour in 0.2×SSC and 0.1% SDS at 55° C., preferably at 62° C. and more preferably at 68° C. A sequence hybridizing with a nucleotide sequence as per SEQ ID No.1 under such washing conditions is a phagolysosomal escape domain encoding nucleotide sequence preferred by the subject invention.

A nucleotide sequence encoding a phagolysosomal escape domain as described above may be directly obtained from a Listeria organism or from any recombinant source e.g. a recombinant E. coli cell containing the corresponding Listeria nucleic acid molecule or a variant thereof as described above.

Preferably, the recombinant nucleic acid molecule encoding for a fusion polypeptide contains a signal peptide encoding sequence. More preferably, the signal sequence is a signal sequence active in Mycobacteria, preferably in M. bovis, e.g. a native M. bovis signal sequence. A preferred example of a suitable signal sequence is the nucleotide sequence coding for the Ag85B signal peptide which is depicted in SEQ ID No.1 from nucleotide 1 to 120.

Further, it is preferred that a peptide linker be provided between the immunogenic domain and the phagolysosomal escape domain. Preferably, said peptide linker has a length of from 5 to 50 amino acids. More preferably, a sequence encoding a linker as shown in SEQ ID No.1 from nucleotide 154 to 210 or a sequence corresponding thereto as regards the degeneration of the genetic code.

The nucleic acid may be located on a recombinant vector. Preferably, the recombinant vector is a prokaryotic vector, i.e.

a vector containing elements for replication or/and genomic integration in prokaryotic cells. Preferably, the recombinant vector carries the nucleic acid molecule of the present invention operatively linked with an expression control sequence. The expression control sequence is preferably an expression control sequence active in Mycobacteria, particularly in *M. bovis*. The vector can be an extrachromosomal vector or a vector suitable for integration into the chromosome. Examples of such vectors are known to the man skilled in the art and, for instance, given in Sambrook et al. supra.

In a further aspect of the present invention a urease-deficient bacterial cell e.g. a *Mycobacterium* cell, preferably an *M. bovis* cell is provided which comprises at least one nucleic acid molecule encoding a phagolysosomal escape peptide or polypeptide. Even if the phagolysosomal escape peptide or polypeptide is not fusioned with an antigen, a surprising improvement of the immunogenic properties is found.

The recombinant bacterial cell which is provided according to this further aspect of the present invention may contain at least one further recombinant, e.g. heterologous nucleic acid molecule encoding a peptide or polypeptide capable of eliciting an immune response in a mammal. Said further immunogenic peptide or polypeptide may be selected from *Mycobacterium* antigens or, in a wider sense, from autoantigens, tumor antigens, pathogen antigens and immunogenic fragments thereof. The nucleic acid molecule coding for the further peptide or polypeptide may be situated on the same vector as the fusion gene. However, it may, for example, also be situated on a different plasmid, independently of the fusion gene, or be chromosomally integrated.

Surprisingly, it was found that a *Mycobacterium* cell according to the present invention has an intracellular persistence in infected cells, e.g. macrophages, which is equal or less than the intracellular persistence of a corresponding native *Mycobacterium* cell which does not contain the recombinant nucleic acid molecule.

The present invention also refers to a pharmaceutical composition comprising as an active agent a cell as defined above, optionally together with pharmaceutically acceptable diluents, carriers and adjuvants. Preferably, the composition is a living vaccine suitable for administration to a mammal, preferably a human. The actually chosen vaccination route depends on the choice of the vaccination vector. Administration may be achieved in a single dose or repeated at intervals. The appropriate dosage depends on various parameters such as the vaccinal vector itself or the route of administration. Administration to a mucosal surface (e.g. ocular, intranasal, oral, gastric, intestinal, rectal, vaginal or urinary tract) or via the parenteral route (e.g. subcutaneous, intradermal, intramuscular, intravenous or intraperitoneal) might be chosen.

Further, the present invention pertains to a method for preparing a recombinant bacterial cell as defined above. According to the first aspect, this method comprises the steps of (i) providing a urease-deficient bacterial cell, particularly a *Mycobacterium* cell, (ii) inserting a recombinant nucleic acid molecule into said bacterial cell, said nucleic acid molecule encoding a fusion polypeptide comprising (a) at least one domain from a polypeptide wherein said domain is capable of eliciting an immune response in a mammal and (b) a phagolysosomal escape domain, and (iii) cultivating the cell obtained according to step (ii) under suitable conditions. Preferably, a cell is obtained which is capable of expressing said nucleic acid molecule. More preferably, the cell is an *M. bovis* cell.

According to the further aspect, this method comprises the step of (i) providing an urease-deficient bacterial cell, particularly a *Mycobacterium* cell, (ii) inserting a recombinant nucleic acid molecule into said bacterial cell, said nucleic acid molecule encoding a phagolysosomal escape peptide or polypeptide, and (iii) cultivating the cell obtained according to (ii) under suitable conditions.

If desired, the method of the present invention comprises inserting at least one further recombinant nucleic acid molecule into the bacterial cell, said further recombinant nucleic acid molecule encoding a peptide or polypeptide capable of eliciting an immune response in a mammal.

Finally, the present invention relates to a method for the preparation of a living vaccine comprising formulating the recombinant cell in a pharmaceutically effective amount with pharmaceutically acceptable diluents, carriers and/or adjuvants.

Due to the high safety of urease-deficient bacterial cells, which was demonstrated in two different animal models (Example 3), the living vaccine of the present invention is particularly suitable for administration to immunodeficient subjects, e.g. subjects suffering from an HIV infection or subjects which are treated with immunosuppressive drugs. In an especially preferred embodiment, the living vaccine of the present invention is used as a tuberculosis vaccine for immunodeficient subjects.

In a further preferred embodiment, the living vaccine is used as a tumor vaccine, e.g. as a vaccine against superficial bladder cancer. In a still further preferred embodiment of the invention, the living vaccine is used in the veterinary field, e.g. as a vaccine against listeriosis, paratuberculosis or bovine tuberculosis.

The invention will be further illustrated by the following figures and sequence listings.

FIG. 1: shows the protective capacity of rBCG ureC Hly in the aerosol model of murine tuberculosis. BALB/c mice were immunized i.v. with 1.times.10.sup.6 CFU rBCG ureC Hly, BCG P ureC or native BCG “Pasteur”. 120 days post vaccination animals were challenged with H37Rv (200 organism/lung) via aerosol. Bacterial load in infected organs (spleen and lung) was assessed 30, 60 and 90 days post challenge. Each line represents 10 animals.

FIG. 2: shows the amount of microorganisms in the lung (FIG. 2*a*) or in the spleen (FIG. 2*b*). Rag1−/− mice were infected with the BCG parental strain (wt) or the rBCG ureC Hly strain (urea-Hly). Bacterial load of the infected organ was assessed 30, 60 and 90 days post infection.

FIG. 3: shows the survival rate of SCID mice infected with BCG “Pasteur” and rBCG delta ureC Hly.

SEQ ID No.1: shows the nucleotide sequence of a nucleic acid molecule according to the present invention.

SEQ ID No.2: shows the corresponding amino acid sequence of the nucleic acid molecule of SEQ ID No.1.

Example 1

Production of Urease-Deficient BCG Hly Strains and Tests in a Mouse Model

1. Inactivation of the Urease Activity of BCG Delta ureC.

In order to improve the protective capacity of a BCG strain containing the Hly protein (rBCG-Hly), the urease activity was deleted.

To obtain a urease-deficient mutant, Reyrat et al. constructed a suicide vector containing a ureC gene disrupted by a kanamycin marker (the aph gene). Two micrograms of this construct were linearized with Sac I and electroporated into *M. bovis* BCG. Kanamycin resistant transformants were screened for urease negative phenotype (cf. Reyrat et al., 1995).

2. Construction of the Mycobacterial E. Coli Shuttle Expression Vector pMV306:Hly.

To transfer the phagosomal escape function (mediated by Hly of *L. monocytogenes* EGD Sv 1/2a), to BCG Pasteur (1173 P$_3$) delta ureC, an *E. coli*-mycobacterial shuttle vector was used. The integrative plasmid pMV306, a precursor of vector pMV361, allows stable chromosomal expression of Hly.

A pILH-1-derived 1.7-kb PstI DNA fragment coding for an hly-hlyA (*E. coli* pHly152-specific hemolysin A) ORF was inserted into PstI site of plasmid pAT261. This resulting gene fusion codes for the expression of secreted proteins directed to the supernatant by the BCG-specific Ag85B signal peptide. The construct was termed pAT261:Hly and its XbaI-SalI DNA expression cassette under transcriptional control of the hsp60 mycobacterial promoter was subsequently used for insertion into the parental pMV306 vector resulting in the construct pMV306:Hly. The DNA sequence of the hly-specific insertion sites in both mycobacterial expression plasmids was analyzed. The mature Hly fusion protein Putatively consists of 30 aa at the N terminus and 52 aa at the C-terminal part of the fusion that partially belong to HlyA of *E. coli*.

3. Protective Capacity in the Mouse Model

Figure 1:
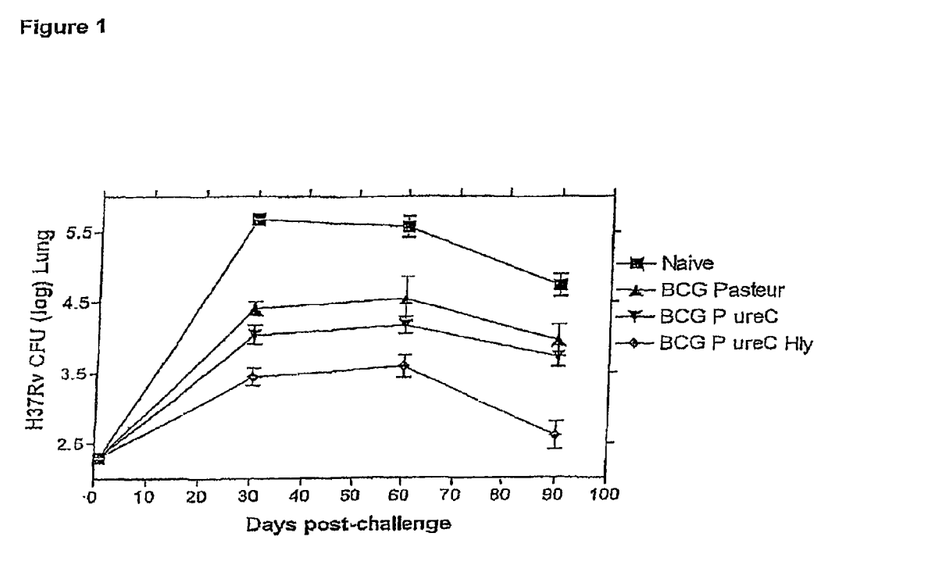

The expression vector pMV306:Hly was transformed into an urease deficient BCG strain pasteur (BCG P ureC). The resultant strain was designated rBCG ureC Hly. The protective capacity of this urease-deficient mycobacterial strain compared to parental BCG Pasteur and BCG Pasteur ureC in a model of murine tuberculosis is shown in FIG. 1. Surprisingly, it was found that rBCG ureC Hly induced improved protection already at early time points (day 30 p.c.) which lasted for the entire observation period (until day 90).

A further long-term protection experiment with rBCG ureC Hly was performed. BALB/c mice were i.v. vaccinated with rBCG ureC Hly, rBCG-Hly or parental BCG and aerosol challenged at day 120 p.i. with *M. tuberculosis* H37Rv. RBCG-Hly and parental BCG induced comparable protection against *M. tuberculosis* H37Rv by day 90. In strong contrast, the rBCG ureC Hly induced improved protection already at early times points beginning at day 30 p.c. Furthermore, this enhanced protection lasted for the entire period of observation and revealed a reduction of *M. tuberculosis* H37Rv load in lung at day 90 p.c. of more than 2 log CFU compared to naive mice, and of more than 1 log CFU compared to mice vaccinated with parental BCG.

Similar results were obtained after challenge with the clinical isolate *M. tuberculosis* Beijing. BALB/c mice were i.v. immunized with rBCG ureC Hly, BCG-Hly or parental BCG and aerosol challenged at day 120 p.i. with *M. tuberculosis* Beijing. Vaccination with BCG ureC Hly induced an improved protection against *M. tuberculosis* Beijing already at early time points (day 30) and lasting for the entire period of observation until day 90 p.c. Compared to vaccination with parental BCG, vaccination with rBCG ureC Hly led to a reduction in the lung of 1 log CFU *M. tuberculosis* Beijing.

Example 2

Long-Term Protection against *M. Tuberculosis* H37Rv in Guinea-Pigs

Since mice are relatively resistant to *M. tuberculosis* infection guinea-pigs as a more susceptible animal model were used to test for vaccination capacity of rBCG ureC Hly. Guinea-pigs were subcutaneously immunized with the respective mycobacterial vaccine strain, rBCG ureC Hly or parental BCG, and weight gain as well as CFU were monitored after aerosol challenge with *M. tuberculosis* H37Rv. Guinea-pigs immunized with rBCG ureC Hly showed similar weight gain than animals vaccinated with the parental BCG strain up to day 120, whereas non-vaccinated animals clearly suffered from TB as indicated by the failure of body weight gain.

Visual examination of lung and spleen prior to CFU analysis showed that tubercles on the surface of both organs from BCG immunized guinea pigs were much larger and more numerous than those from BCG ureC Hly-vaccinated animals.

Example 3

Safety Evaluation of BCG ureC Hly

Figure 2A:
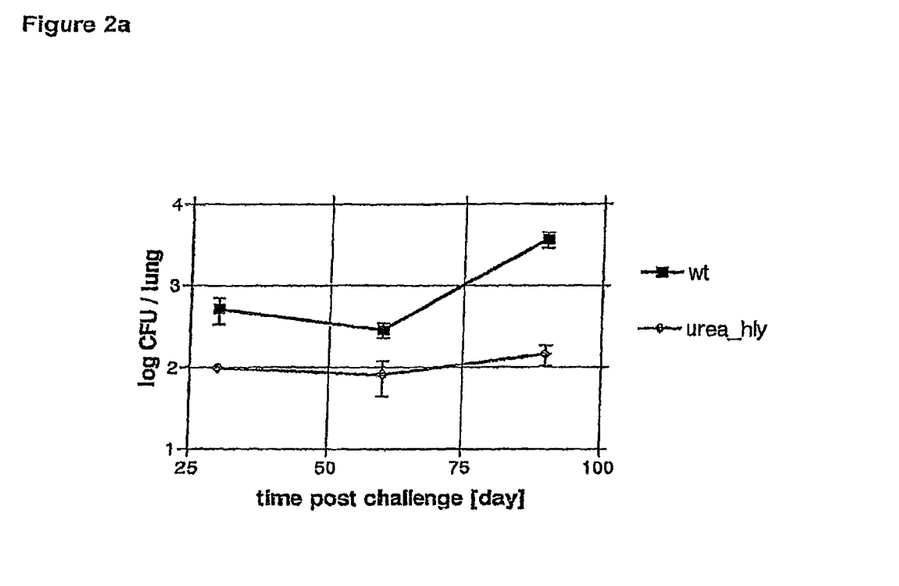
Figure 2B:
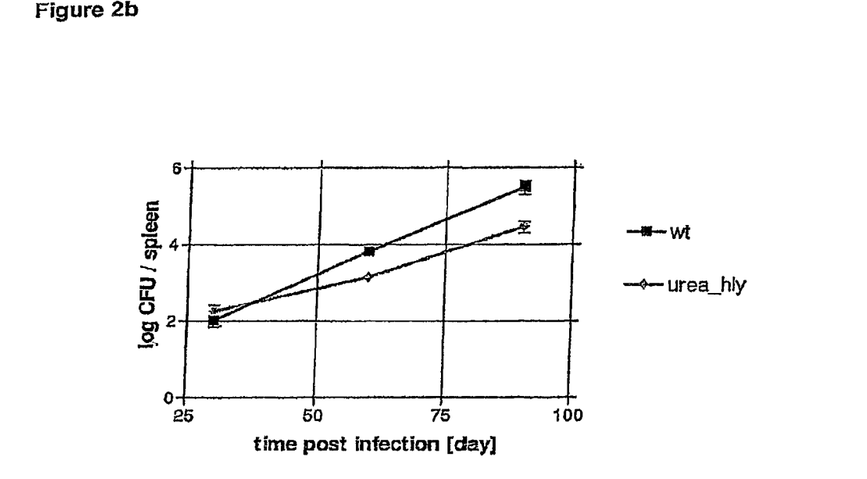

Rag1-/-mice deficient in T- and B-cells were infected with $10^6$ microorganisms of the BCG parental strain (wt) or the rBCG ureC Hly strain. The presence of microorganisms in lung and spleen was monitored. Significantly reduced CFU of rBCG ureC Hly were observed in the lung (FIG. 2a). In the spleen, slightly reduced CFU were observed after infection with rBCG ureC Hly compared to infection with parental BCG (FIG. 2b).

Further, the safety of BCG ureC Hly was tested in immunodeficient SCID mice.

Figure 3:
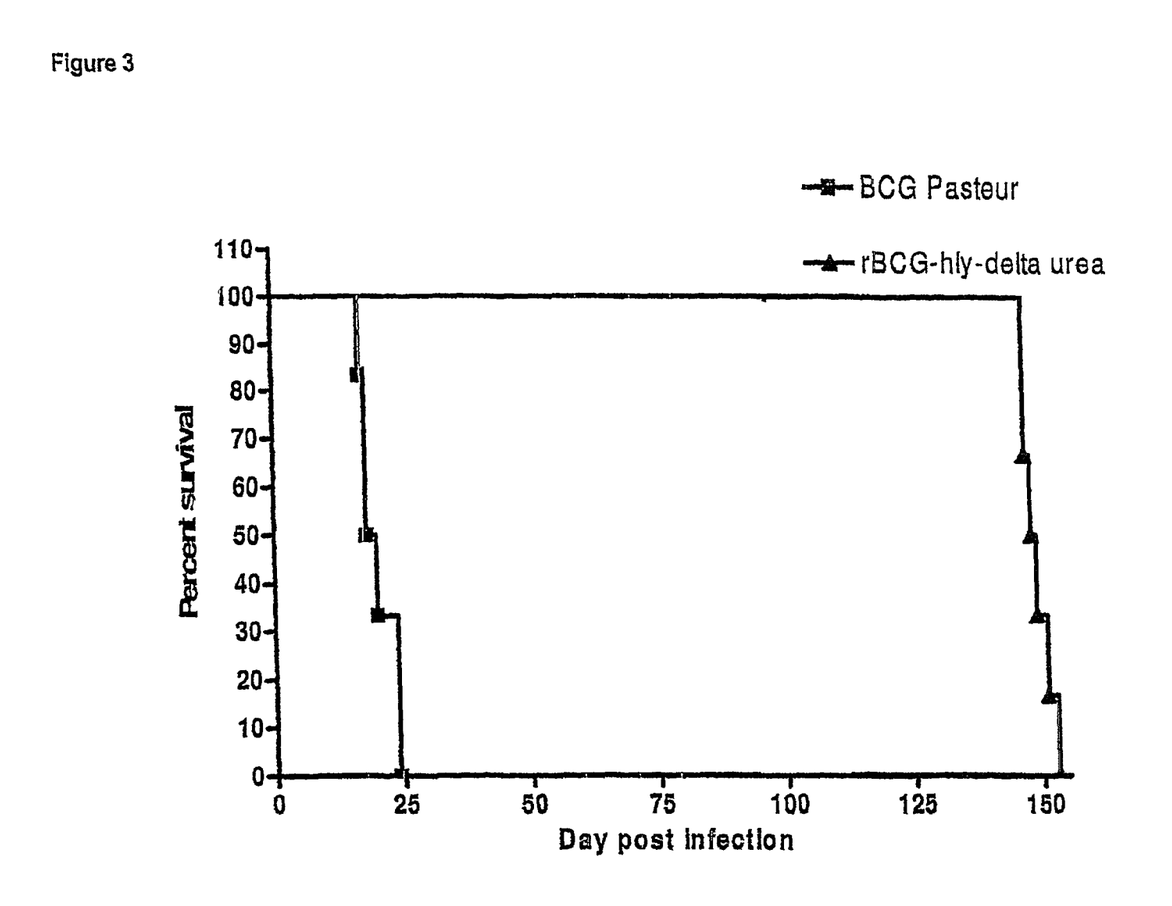

For this purpose, SCID mice were intravenously inoculated with $10^7$-$10^8$ microorganisms of rBCG ureC Hly or the parental BCG strain. Whereas SCID mice inoculated with the parental strain died by day 25 p.i., mice inoculated with rBCG ureC Hly survived until day 150 p.i. (FIG. 3).

These experiments demonstrated that BCG ureC Hly has a higher safety compared to the parental BCG strain.

REFERENCES

Aidoo, M., Lalvani, A., Allsopp, C. E. M. et al. (1995), Identification of conserved antigenic components for a cytotoxic T lymphocyte-inducing vaccine against malaria, The Lancet 345: 1003.

Andersen, P. (1994), Effective vaccination of mice against *Mycobacterium tuberculosis* infection with a soluble mixture of secreted Mycobacterial protein, Infect. Immun. 62: 2536-2544.

Andersen, P., Andersen, A. B., Sorensen, A. L. and Nagai, S. (1995), Recall of long-lived immunity to *Mycobacterium tuberculosis* infection in mice, J. Immunol. 154: 3359.

Berche, P., Gaillard, J. L., and Sansonetti, P. J. (1987), Intracellular growth of *L. monocytogenes* as a prerequisite for in vivo induction of T cell-mediated immunity, J. Immunol. 138: 2266-2276.

Bielecki, J., Youngman, P., Connelly, P., and Portnoy, D. A. (1990), *Bacillus subtilis* expressing a hemolysin gene from *Listeria monocytogenes* can grow in mammalian cells, Nature 354: 175-176.

Blander, S. J. and Horwitz, M. A. (1991), Vaccination with a major secretory protein of *Legionella* induces humoral and cell-mediated immune responses and protective immunity across different serogroups of *Legionella pneumophila* and different species of *Legionella*, J. Immunol. 147: 285.

Bosch, F. X., Durst, M., Schwarz, E., Boukamp, P., Fusenig, N. E. and zur Hausen, H. (1991), The early genes E6 and E7 of cancer associated human papilloma viruses as targets of tumor suppression?, Behring Inst. Mitt. 108.

Bulow, R. and Boothroyd, J. C. (1991), Protection of mice from fatal *Toxoplasma gondii* infection by immunization with p30 antigen in liposomes, J. Immunol. 147: 3496.

Clemens, D. L., and Horwitz, M. A. (1996), The *Mycobacterium tuberculosis* phagosome interacts with early endosomes and is accessible to exogenously administered transferrin, J. Exp. Med. 184: 1349-1355.

Clemens, D. L., Lee B. Y., Horwitz, M. A. (1995), Purification, characterization, and genetic analysis of *Mycobacterium tuberculosis* urease, a potentially critical determinant of host-pathogen interaction. J. Bacteriol. 1995 177:5644-5652.

Darji, A., Chakraborty, T., Wehland, J., and Weiss, S. (1996), Listeriolysin generates a route for the presentation of exogenous antigens by major histocompatibility complex class I, Eur. J. Immunol. 25: 2967-2971.

Domann, E., and Chakraborty, T. (1989), Nucleotide sequence of the listeriolysin gene from a *Listeria monocytogenes* serotype 1/2a strain, Nucleic Acids Res. 17: 6406.

Flesch, I., Hess, J. H., Oswald, I. P., and Kaufmann, S. H. E. (1994), Growth inhibition of *Mycobacterium bovis* by IFN-γ stimulated macrophages: regulation by endogenous tumor necrosis factor-α and by IL-10, Int. Immunol. 6: 693-700.

Flynn, J. L., Goldstein, M. M., Triebold, K. J., Koller, B., and Bloom, B. R. (1992), Major histocompatibility complex class I-restricted T cells are required for resistance to *Mycobacterium tuberculosis* infection, Proc. Natl. Acad. Sci. USA 89: 12013-12017.

Fu, T. M., Friedman, A., Ulmer, J. B., Liu, M. A. and Donnelly, J. J. (1997), Protective cellular immunity: cytotoxic T-lymphocyte responses against dominant and recessive epitopes of influenza virus nucleoprotein induced DNA immunization, J. Virol. 71: 2715.

Gaillard, J. L., Berche, P., Mounier, J., Richard, S., and Sansonetti, P. J. (1987), In vitro model of penetration and intracellular growth of *Listeria monocytogenes* in the human enterocyte-like cell line Caco-2, Infect. Immun. 55: 2822-2829.

Gentschev, I., Sokolovic, Z., Mollenkopf, H.-J., Hess, J., Kaufmann, S. H. E., Kuhn, M., Krohne, G. F., and Goebel, W. (1995), *Salmonella* secreting active listeriolysin changes its intracellular localization, Infect. Immun. 63: 4202-4205.

Grange, J. M. (1996), Epidemiological aspects of drug resistance, in Mycobacteria and human disease, Arnold, London, pp. 124-125.

Haas, G., Plikat, U., Debre, P., Lucchiari, M., Katlama, C., Dudoit, Y., Bonduelle, O., Bauer, M., Ihlenfeldt, H. G., Jung, G., Maier, B., Meyerhans, A. and Autran, B. (1996), Dynamics of viral variants in HIV-1 Nef and specific cytotoxic T lymphocytes in vivo, J. Immunol. 157: 4212.

Harboe, M., Oettinger, T., Wiker, H. G. et al. (1996), Evidence for occurrence of the ESAT-6 protein in *Mycobacterium tuberculosis* and virulent *Mycobacterium bovis* and for its absence in *Mycobacterium bovis* BCG, Infect. Immun. 64: 16.

Harrer, T., Harrer, E., Kalams, S. A., Barbosa, P., Trocha, A., Johnson, R. P., Elbeik, T., Feinberg, M. B., Buchbinder, S. P. and Walker, B. D. (1996), Cytotoxic T lymphocytes in asymptomatic long-term nonprogressing HIV-1 infection. Breadth and specificity of the response and relation to in vivo viral quasispecies in a person with prolonged infection and low viral load, J. Immunol. 156: 2616.

Harth, G., Lee, B.-Y., Wang. J., Clemens, D. L., and Horwitz, M. A. (1996), Novel insights into the genetics, biochemistry, and immunocytochemistry of the 30-kilodalton major extracellular protein of *Mycobacterium tuberculosis*, Infect. Immun. 64: 3038-3047.

Hess, J., Wels, W., Vogel, M., and Goebel, W. (1986), Nucleotide sequence of plasmid-encoded hemolysin determinant and its comparison with a corresponding chromosomal hemolysin sequence, FEMS Lett. 34: 1-11.

Hess, J., and Kaufmann, S. H. E. (1993), Vaccination strategies against intracellular microbes, FEMS Microbiol. Immunol. 7: 95-103.

Hess, J., Gentschev, I., Miko, D., Welzel, M., Ladel, C., Goebel, W., and Kaufmann, S. H. E. (1996), Superior efficacy of secreted over somatic p60 or listeriolysin antigen display in recombinant *Salmonella* vaccine induced protection against listeriosis, Proc. Natl. Acad. Sci. USA 93: 1458-1463.

Hess, J., and Kaufmann, S. H. E. (1997), Principles of cell-mediated immunity underlying vaccination strategies against intracellular pathogens, in Host Response to Intracellular Pathogens, S. H. E. Kaufmann (ed), R.G. Landes Co., Austin, pp. 75-90.

Hess J., Miko D., Catic A., Lehmensiek V., Russell D G., Kaufmann S H., (1998), *Mycobacterium bovis* Bacille Calmette-Guerin strains secreting listeriolysin of *Listeria monocytogenes*. Proc Natl Acad Sci USA. 95(9):5299-304.

Horwitz, M. A., Lee, B.-W. E., Dillon, B. J., and Harth, G. (1995), Protective immunity against tuberculosis induced by vaccination with major extracellular proteins of *Mycobacterium tuberculosis*, Proc. Natl. Acad. Sci. USA 92: 1530-1534.

Houbiers, J. G. A., Nijman, H. W., van der Burg, S. H., Drijfhout, J. W., Kenemans, P., van de Velde, C. J. H., Brand, A., Momburg, F., Kast, W. M. and Melief, C. J. M. (1993), In vitro induction of human cytotoxic T lymphocyte responses against peptides of mutant and wild-type p53, Eur. J. Immunol. 23: 2072.

Huygen, K., Content, J., Denis, O., Montgomery, D. L., Yawman, A. M., Deck, R. R., DeWitt, C. M., Orme, I. M., Baldwin, S., D'Souza, C., Drowart, A., Lozes, E., Vandenbussche, P., Van Vooren, J.-P., Liu, M. A., and Ulmer, J. B. (1996), Immunogenicity and protective efficacy of a tuberculosis DNA vaccine, Nat. Med. 2: 893-898.

Kaufmann, S. H. E. (1993), Immunity to intracellular bacteria, Annu. Rev. Immunol. 11: 129-163.

Khan, I. A., Ely, K. H. and Kasper, L. H. (1991), A purified parasite antigen (p30) mediates CD8 T cell immunity against fatal *Toxoplasma gondii* infection in mice, J. Immunol. 147: 3501.

King, C. H., Mundayoor, S., Crawford, J. T. and Shinnik, T. M. (1993), Expression of contact-dependent cytolytic activity by *Mycobacterium tuberculosis* and isolation of the genomic locus that encodes the activity, Infect. Immun. 61: 2708-2712.

Kochi, A. (1991), The global tuberculosis situation and the new control strategy of the World Health Organization, Tubercle 72: 1-6.

Ladel, C. H., Daugelat, S., and Kaufmann, S. H. E. (1995), Immune response to *Mycobacterium bovis* bacille Calmette Guérin infection in major histocompatibility complex class I- and II-deficient knock-out mice: contribution of CD4 and CD8 T cells to acquired resistance, Eur. J. Immunol. 25: 377-384.

Laemmli, U. K. (1970), Cleavage of structural proteins during the assembly of the head of bacteriophage T4, Nature 227: 680-685.

Langermann, S., Palaszynski, S. R., Burlein, J. E., Koenig, S., Hanson, M. S., Briles, D. E., and Stover, C. K. (1994), Protective humoral response against pneumococcal infection in mice elicited by recombinant Bacille Calmette-Guérin vaccines expressing pneumococcal surface protein A., J. Exp. Med. 180: 2277-2286.

Matsui, M., Moots, R. J., Warburton, R. J., Peace-Brewer, A., Tussey, L. G., Quinn, D. G., McMichael, A. J. and J. A. Frelinger (1995), Genetic evidence for differences between intracellular peptides of influenza A matrix peptide-specific CTL recognition, J. Immunol. 154: 1088.

Matsuo, K., Yamaguchi, R., Yamazaki, A., Tasaka, H., Terasaka, K., and Yamada, T. (1990), Cloning and expression of the *Mycobacterium bovis* BCG gene for extracellular alpha antigen, J. Bacteriol. 170: 3847-3854.

Mazzaccaro, R. Z., Gedde, M., Jensen, E. R., Van Santen, H. M., Ploegh H. L., Rock, K. L., and Bloom, B. R. (1996), Major histocompatibility class I presentation of soluble antigen facilitated by *Mycobacterium tuberculosis* infection, Proc. Natl. Acad. Sci. USA 93: 11786-11791.

McDonough, K. A., Kress, Y., and Bloom, B. R. (1993), Pathogenesis of tuberculosis: Interaction of *Mycobacterium tuberculosis* with macrophages, Infect. Immun. 61: 2763-2773.

Murray, P. J., Aldovini, A., and Young, R. A. (1996), Manipulation and potentiation of anti-mycobacterial immunity using recombinant bacille Calmette-Guérin strains that secrete cytokines, Proc. Natl. Acad. Sci. USA 93: 934-939.

Nato, F., Reich, K., Lhopital, S., Rouye, S., Geoffroy, C., Mazie, J. C., and Cossart, P. (1991), Production and characterization of neutralizing and non-neutralizing monoclonal antibodies against listeriolysin O., Infect. Immun. 59: 4641-4646.

Portnoy, D. A., Jacks, P. S., and Hinrichs, D. J. (1988), Role of hemolysin for the intracellular growth of *Listeria monocytogenes*, J. Exp. Med. 167: 1459-1471.

Reyrat J. M., Berthet F. X., Gicquel B., (1995) The urease locus of *Mycobacterium tuberculosis* and its utilization for the demonstration of allelic exchange in *Mycobacterium bovis* bacillus Calmette-Guerin. Proc Natl Acad Sci USA. 92(19):8768-72.

Roche, P. W., Triccas, J. A., and Winter, N. (1995), BCG vaccination against tuberculosis: past disappointments and future hopes, Trends Microbiol. 3: 397-401.

Russell, D. G. (1995), *Mycobacterium* and *Leishmania*: stowaways in the endosomal network. Trends in Cell Biology 5: 125-128.

Sambrook, J., Fritsch, E. F., and Maniatis, T. (1989), Molecular cloning: a laboratory manual, 2nd edition, Cold Spring Harbor Laboratory Press, New York.

Schoel, B., Welzel, M., and Kaufmann, S. H. E. (1994), Hydrophobic interaction chromatography for the purification of cytolytic bacterial toxins, J. Chromatography A 667: 131-139.

Sorensen, A. L., Nagai, S., Houen, G., Andersen, P. and Andersen, A. B. (1995), Purification and characterization of a low-molecular-mass-T-cell antigen secreted by *Mycobacterium tuberculosis*, Infect Immun. 63: 1710.

Stover, C. K., Bansal, G. P., Hanson, M. S. Burlein, J. E., Palaszynski, S. R., Young, J. F., Koenig, S., Young, D. B., Sadziene, A., Barbour, A. G. (1993), Protective immunity elicited by recombinant Bacille Calmette Guérin (BCG) expressing outer surface protein A (OspA) lipoprotein: A candidate lyme disease vaccine, J. Exp. Med. 178: 197-209.

Stover, C. K., de is Cruz, V. F., Fuerst, T. R., Burlein, J. E., Benson, L. A., Bennett, L. T., Bansal, G. P., Young, J. F., Lee, M. H., Hatfull, G. F., Snapper, S. B., Barletta, R. G., Jacobs, W. R., Jr., and Bloom, B. R. (1991), New use of BCG for recombinant vaccines, Nature 351: 456-460.

Sturgill-Koszycki, S., Schlesinger, P. H., Chakraborty, P., Haddix, P. L., Collins, H. L., Fok, A. K., Allen, R. D., Gluck, S. L., Heuser, J. and Russell, D. G. (1994), Lack of acidification in *Mycobacterium* phagosomes produced by exclusion of the vesicular proton-ATPase, Science 263: 678-681.

Towbin, H., Staehelin, T., and Gordon, J. (1979), Electrophoretic transfer of proteins from polyacrylamide gels to nitrocellulose sheets: procedure and some applications, Proc. Natl. Acad. Sci. USA 76: 4350-4354.

Tsuchiya, S., Kobayashi, Y., Goto, Y., Okumura, H., Nakae, S., Konno, T., and Tada, K. (1982), Induction of maturation in cultured human monocytic leukemia cells by a phorbol diester, Cancer Res. 42: 1530-1536.

Tweten, R. K. (1995), Pore-forming toxins of gram-positive bacteria, in Virulence Mechanisms of Bacterial Pathogens, J. A. Roth et al. (ed), American Society for Microbiology, Washington, D.C., pp. 207-228.

van Elsas, A., van der Burg, S. H., van der Minne, C. E., Borghi, M., Mourer, J. S., Melief, C. J. M. and Schrier, P. I. (1996), Peptide-pulsed dendritic cells induce tumoricidal cytotoxic T lymphocytes from healthy donors against stably HLA A*0201-binding peptides from Melan-A/MART-1 self antigen, Eur. J. Immunol. 26: 1683.

The invention claimed is:

1. A *Mycobacterium* cell which is urease-deficient and which comprises at least one recombinant nucleic acid molecule encoding a phagolysosomal escape peptide or polypeptide.

2. The cell of claim 1, further comprising at least one second recombinant nucleic acid molecule encoding a peptide or polypeptide capable of eliciting an immune response in a mammal, wherein said cell is capable of secreting a polypeptide encoded by said at least one second recombinant nucleic acid molecule.

3. The cell of claim 1, which is a *Mycobacterium bovis* cell.

4. The cell of claim 1, wherein at least one cellular urease subunit-encoding nucleic acid sequence is inactivated.

5. The cell of claim 4, wherein the urease-deficient bacterial strain is obtained by a deletion and/or insertion of one or several nucleotides in the urease subunit encoding nucleic acid sequences and/or the expression control sequences thereof.

6. The cell of claim 4, wherein at least one cellular urease C subunit-encoding sequence is inactivated.

7. The cell of claim 6, wherein the urease-deficient bacterial strain is obtained by a deletion and/or insertion of one or several nucleotides in the at least one cellular urease C subunit encoding nucleic acid sequence and/or their expression control sequence.

8. The cell of claim 1, wherein said phagolysosomal escape peptide is a *Listeria* phagolysosomal escape domain.

9. The cell of claim 1, wherein said phagolysosomal peptide is encoded by a nucleic acid molecule comprising a sequence selected from:

(a) a nucleotide sequence consisting of nucleotide 211-1722 as shown in SEQ ID No.1, (b) a nucleotide sequence which encodes for the same amino acid sequence as the sequence from (a), and (c) a nucleotide sequence hybridizing under stringent conditions with the sequence from (a) or (b), wherein said stringent conditions correspond to a condition in which a positive hybridization signal can be observed after washing for an hour with at least 0.2×SSC and 0.1% SDS at a temperature of at least 55° C.

10. The cell of claim 1, further comprising at least one second recombinant nucleic acid molecule encoding a peptide or polypeptide capable of eliciting an immune response in a mammal, wherein the peptide or polypeptide capable of eliciting an immune response is a peptide or polypeptide suitable for MHC class I-restricted antigen recognition.

11. The cell of claim 1, further comprising at least one second recombinant nucleic acid molecule encoding a peptide or polypeptide capable of eliciting an immune response in a mammal, wherein the peptide or polypeptide capable of eliciting an immune response is a peptide or polypeptide capable of eliciting a T cell-mediated immune response.

12. The cell of claim 1, further comprising at least one second recombinant nucleic acid molecule, encoding a peptide or polypeptide capable of eliciting an immune response in a mammal, that is a *Mycobacterium* polypeptide or a fragment thereof.

13. The cell of claim 12, wherein the peptide or polypeptide capable of eliciting an immune response is selected from the *Mycobacterium* antigens Ag85B (*M. tuberculosis*), Ag85B (*M. bovis*), Ag85A (*M. tuberculosis*) and ESAT-6 (*M. tuberculosis*) or an immunogenic fragment thereof.

14. The cell of claim 1, further comprising at least one second recombinant nucleic acid molecule encoding a peptide or polypeptide capable of eliciting an immune response in a mammal, that is located on a vector.

15. The cell of claim 1, further comprising at least one second recombinant nucleic acid molecule encoding a peptide or polypeptide capable of eliciting an immune response in a mammal that is chromosomally integrated.

16. The cell of claim 1, further comprising a signal peptide sequence which precedes the at least one recombinant nucleic acid sequence encoding the phagolysosomal escape peptide or polypeptide.

17. The cell of claim 16, wherein the signal sequence is a nucleotide sequence coding for the Ag85B signal peptide.

18. The cell of claim 1, which has an intracellular persistence in infected macrophages which is equal to or less than the intracellular persistence of a native *Mycobacterium* cell.

19. A pharmaceutical composition comprising as an active agent a *Mycobacterium* cell of claim 1 together with at least one pharmaceutically acceptable diluent, carrier, adjuvant, or combination thereof.

20. A method for the preparation of a living vaccine comprising mixing a pharmaceutically effective amount of the *Mycobacterium* cell of claim 1 with at least one pharmaceutically acceptable diluent, carrier, adjuvant or combination thereof.

21. A method for preparing a recombinant *Mycobacterium* cell of claim 1 comprising the steps:
(i) providing a urease-deficient *Mycobacterium* cell;
(ii) inserting a recombinant nucleic acid molecule into said *Mycobacterium* cell, said nucleic acid molecule encoding a phagolysosomal escape peptide or polypeptide; and
(iii) cultivating the cell obtained according to (ii) under suitable conditions.

22. The method of claim 21, wherein said *Mycobacterium* cell is a *M. bovis* cell.

23. The method of claim 21 further comprising inserting at least one second recombinant nucleic acid molecule into the *Mycobacterium* cell, said second recombinant nucleic acid molecule encoding a peptide or polypeptide capable of eliciting an immune response in a mammal.

24. A method of treating a mammal having tuberculosis, comprising administering to the mammal the *Mycobacterium* cell of claim 2 which comprises at least one recombinant nucleic acid molecule encoding a phagolysosomal escape peptide or polypeptide and at least one second recombinant nucleic acid molecule encoding a peptide or polypeptide that elicits an immune response in a mammal, in a pharmaceutically effective amount, wherein said peptide or polypeptide capable of eliciting an immune response to tuberculosis is selected from the group of bacterial antigens and immunogenic fragments thereof that elicit an immune response to tuberculosis.

25. The method of claim 24, wherein the peptide or polypeptide capable of eliciting an immune response to tuberculosis is selected from the group consisting of *Mycobacterium* antigens Ag856 (*M. tuberculosis*), Ag85B (*M. bovis*), Ag85A (*M. tuberculosis*) and ESAT-6 (*M. tuberculosis*) or an immunogenic fragment thereof that elicits an immune response to tuberculosis.

26. A method of preventing tuberculosis in a mammal, comprising administering to the mammal a *Mycobacterium* cell according to claim 2 which comprises at least one recombinant nucleic acid molecule encoding a phagolysosomal escape peptide or polypeptide and at least one second recombinant nucleic acid molecule encoding a peptide or polypeptide that elicits an immune response in a mammal, in a pharmaceutically effective amount, wherein said peptide or polypeptide capable of eliciting an immune response to tuberculosis is selected from the group consisting of bacterial antigens and immunogenic fragments thereof that elicit an immune response to tuberculosis.

27. The method of claim 26, wherein the peptide or polypeptide capable of eliciting an immune response to tuberculosis is selected from the group consisting of *Mycobacterium* antigens Ag85B (*M. tuberculosis*), Ag85B (*M. bovis*), Ag85A (*M. tuberculosis*) and ESAT-6 (*M. tuberculosis*) or an immunogenic fragment thereof that elicits an immune response to tuberculosis.

28. A method of eliciting an immune response to a disease state which is now or later may be in a mammal, comprising administering to said mammal a *Mycobacterium* cell which is urease-deficient and which comprises at least one recombinant nucleic acid molecule encoding a phagolysosomal escape peptide or polypeptide and at least one second recombinant nucleic acid molecule encoding a peptide or polypeptide that elicits an immune response to said disease state in a mammal, in a pharmaceutically effective amount, wherein said peptide or polypeptide that elicits an immune response to said disease state is selected from the group of autoantigens, tumor antigens, virus antigens, parasite antigens, bacterial antigens, and immunogenic fragments thereof that elicit an immune response to said disease state.

29. The method of claim 28, wherein the mammal is immunodeficient.

30. The method of claim 29, wherein the disease state is a HIV infection, wherein the peptide or polypeptide capable of eliciting an immune response to said HIV infection is selected from the group consisting of a HIV antigen, p17, p24, RT and Env.

31. The method of claim 28, wherein disease state is a tumor, and wherein the peptide or polypeptide capable of eliciting an immune response is a tumor antigen that elicits an immune response to said tumor.

32. The method of claim 28, wherein the disease state is superficial bladder cancer, and wherein the peptide or polypeptide capable of eliciting an immune response is a tumor antigen that elicits an immune response to said superficial bladder cancer.

33. The method of claim 28, wherein the mammal is an animal.

34. The method of claim 28, wherein the mammal is a human.

35. The method of claim 28, wherein the tumor antigen is selected from the group consisting of p53 tumor suppressor gene product that elicits an immune response to said tumor, a melanocyte differentiation antigen that elicits an immune response to said tumor, Melan-A/MART-1 that elicits an immune response to said tumor, and gp100 that elicits an immune response to said tumor.

* * * * *

SEQUENCE LISTING

```
<160> NUMBER OF SEQ ID NOS: 2

<210> SEQ ID NO 1
<211> LENGTH: 1881
<212> TYPE: DNA
<213> ORGANISM: Mycobacterium
<220> FEATURE:
<221> NAME/KEY: CDS
<222> LOCATION: (1)..(1878)

<400> SEQUENCE: 1 atg aca gac gtg agc cga aag att cga gct tgg gga cgc cga ttg atg       48
Met Thr Asp Val Ser Arg Lys Ile Arg Ala Trp Gly Arg Arg Leu Met
1               5                   10                  15 atc ggc acg gca gcg gct gta gtc ctt ccg ggc ctg gtg ggg ctt gcc       96
Ile Gly Thr Ala Ala Ala Val Val Leu Pro Gly Leu Val Gly Leu Ala
            20                  25                  30
```

```
ggc gga gcg gca acc gcg ggc gcg ttc tcc cgg ccg ggg ctg ccg gtc      144
Gly Gly Ala Ala Thr Ala Gly Ala Phe Ser Arg Pro Gly Leu Pro Val
        35                  40                  45 gag tac ctg cag tct gca aag caa tcc gct gca aat aaa ttg cac tca      192
Glu Tyr Leu Gln Ser Ala Lys Gln Ser Ala Ala Asn Lys Leu His Ser
 50                  55                  60 gca gga caa agc acg aaa gat gca tct gca ttc aat aaa gaa aat tca      240
Ala Gly Gln Ser Thr Lys Asp Ala Ser Ala Phe Asn Lys Glu Asn Ser
 65                  70                  75                  80 att tca tcc atg gca cca cca gca tct ccg cct gca agt cct aag acg      288
Ile Ser Ser Met Ala Pro Pro Ala Ser Pro Pro Ala Ser Pro Lys Thr
                 85                  90                  95 cca atc gaa aag aaa cac gcg gat gaa atc gat aag tat ata caa gga      336
Pro Ile Glu Lys Lys His Ala Asp Glu Ile Asp Lys Tyr Ile Gln Gly
            100                 105                 110 ttg gat tac aat aaa aac aat gta tta gta tac cac gga gat gca gtg      384
Leu Asp Tyr Asn Lys Asn Asn Val Leu Val Tyr His Gly Asp Ala Val
                115                 120                 125 aca aat gtg ccg cca aga aaa ggt tac aaa gat gga aat gaa tat att      432
Thr Asn Val Pro Pro Arg Lys Gly Tyr Lys Asp Gly Asn Glu Tyr Ile
130                 135                 140 gtt gtg gag aaa aag aag aaa tcc atc aat caa aat aat gca gac att      480
Val Val Glu Lys Lys Lys Lys Ser Ile Asn Gln Asn Asn Ala Asp Ile
145                 150                 155                 160 caa gtt gtg aat gca att tcg agc cta acc tat cca ggt gct ctc gta      528
Gln Val Val Asn Ala Ile Ser Ser Leu Thr Tyr Pro Gly Ala Leu Val
                165                 170                 175 aaa gcg aat tcg gaa tta gta gaa aat caa cca gat gtt ctc cct gta      576
Lys Ala Asn Ser Glu Leu Val Glu Asn Gln Pro Asp Val Leu Pro Val
                180                 185                 190 aaa cgt gat tca tta aca ctc agc att gat ttg cca ggt atg act aat      624
Lys Arg Asp Ser Leu Thr Leu Ser Ile Asp Leu Pro Gly Met Thr Asn
            195                 200                 205 caa gac aat aaa atc gtt gta aaa aat gcc act aaa tca aac gtt aac      672
Gln Asp Asn Lys Ile Val Val Lys Asn Ala Thr Lys Ser Asn Val Asn
210                 215                 220 aac gca gta aat aca tta gtg gaa aga tgg aat gaa aaa tat gct caa      720
Asn Ala Val Asn Thr Leu Val Glu Arg Trp Asn Glu Lys Tyr Ala Gln
225                 230                 235                 240 gct tat cca aat gta agt gca aaa att gat tat gat gac gaa atg gct      768
Ala Tyr Pro Asn Val Ser Ala Lys Ile Asp Tyr Asp Asp Glu Met Ala
                245                 250                 255 tac agt gaa tca caa tta att gcg aaa ttt ggt aca gca ttt aaa gct      816
Tyr Ser Glu Ser Gln Leu Ile Ala Lys Phe Gly Thr Ala Phe Lys Ala
                260                 265                 270 gta aat aat agc ttg aat gta aac ttc ggc gca atc agt gaa ggg aaa      864
Val Asn Asn Ser Leu Asn Val Asn Phe Gly Ala Ile Ser Glu Gly Lys
                275                 280                 285 atg caa gaa gaa gtc att agt ttt aaa caa att tac tat aac gtg aat      912
Met Gln Glu Glu Val Ile Ser Phe Lys Gln Ile Tyr Tyr Asn Val Asn
            290                 295                 300 gtt aat gaa cct aca aga cct tcc aga ttt ttc ggc aaa gct gtt act      960
Val Asn Glu Pro Thr Arg Pro Ser Arg Phe Phe Gly Lys Ala Val Thr
305                 310                 315                 320 aaa gag cag ttg caa gcg ctt gga gtg aat gca gaa aat cct cct gca     1008
Lys Glu Gln Leu Gln Ala Leu Gly Val Asn Ala Glu Asn Pro Pro Ala
                325                 330                 335 tat atc tca agt gtg gcg tat ggc cgt caa gtt tat ttg aaa tta tca     1056
Tyr Ile Ser Ser Val Ala Tyr Gly Arg Gln Val Tyr Leu Lys Leu Ser
            340                 345                 350
```

| | | | | | | | | | | | | | | | |
|---|---|---|---|---|---|---|---|---|---|---|---|---|---|---|---|
| act | aat | tcc | cat | agt | act | aaa | gta | aaa | gct | gct | ttt | gat | gct | gcc | gta | 1104 |
| Thr | Asn | Ser | His | Ser | Thr | Lys | Val | Lys | Ala | Ala | Phe | Asp | Ala | Ala | Val | |
| | | 355 | | | | 360 | | | | 365 | | | | | | |
| agc | gga | aaa | tct | gtc | tca | ggt | gat | gta | gaa | cta | aca | aat | atc | atc | aaa | 1152 |
| Ser | Gly | Lys | Ser | Val | Ser | Gly | Asp | Val | Glu | Leu | Thr | Asn | Ile | Ile | Lys | |
| | 370 | | | | 375 | | | | 380 | | | | | | | |
| aat | tct | tcc | ttc | aaa | gcc | gta | att | tac | gga | ggt | tcc | gca | aaa | gat | gaa | 1200 |
| Asn | Ser | Ser | Phe | Lys | Ala | Val | Ile | Tyr | Gly | Gly | Ser | Ala | Lys | Asp | Glu | |
| 385 | | | | 390 | | | | 395 | | | | 400 | | | | |

(table continues with remaining rows, position numbers, and nucleotide counts)

| | | | | | | | | | | | | | | | |
|---|---|---|---|---|---|---|---|---|---|---|---|---|---|---|---|
| gtt | caa | atc | atc | gac | ggc | aac | ctc | gga | gac | tta | cgc | gat | att | ttg | aaa | 1248 |
| Val | Gln | Ile | Ile | Asp | Gly | Asn | Leu | Gly | Asp | Leu | Arg | Asp | Ile | Leu | Lys | |
| | | | 405 | | | | 410 | | | | 415 | | | | | |
| aaa | ggc | gct | act | ttt | aat | cga | gaa | aca | cca | gga | gtt | ccc | att | gct | tat | 1296 |
| Lys | Gly | Ala | Thr | Phe | Asn | Arg | Glu | Thr | Pro | Gly | Val | Pro | Ile | Ala | Tyr | |
| | | 420 | | | | 425 | | | | 430 | | | | | | |
| aca | aca | aac | ttc | cta | aaa | gac | aat | gaa | tta | gct | gtt | att | aaa | aac | aac | 1344 |
| Thr | Thr | Asn | Phe | Leu | Lys | Asp | Asn | Glu | Leu | Ala | Val | Ile | Lys | Asn | Asn | |
| | | 435 | | | | 440 | | | | 445 | | | | | | |
| tca | gaa | tat | att | gaa | aca | act | tca | aaa | gct | tat | aca | gat | gga | aaa | att | 1392 |
| Ser | Glu | Tyr | Ile | Glu | Thr | Thr | Ser | Lys | Ala | Tyr | Thr | Asp | Gly | Lys | Ile | |
| 450 | | | | 455 | | | | 460 | | | | | | | | |
| aac | atc | gat | cac | tct | gga | gga | tac | gtt | gct | caa | ttc | aac | att | tct | tgg | 1440 |
| Asn | Ile | Asp | His | Ser | Gly | Gly | Tyr | Val | Ala | Gln | Phe | Asn | Ile | Ser | Trp | |
| 465 | | | | 470 | | | | 475 | | | | 480 | | | | |
| gat | gaa | gta | aat | tat | gat | cct | gaa | ggt | aac | gaa | att | gtt | caa | cat | aaa | 1488 |
| Asp | Glu | Val | Asn | Tyr | Asp | Pro | Glu | Gly | Asn | Glu | Ile | Val | Gln | His | Lys | |
| | | | 485 | | | | 490 | | | | 495 | | | | | |
| aac | tgg | agc | gaa | aac | aat | aaa | agc | aag | cta | gct | cat | ttc | aca | tcg | tcc | 1536 |
| Asn | Trp | Ser | Glu | Asn | Asn | Lys | Ser | Lys | Leu | Ala | His | Phe | Thr | Ser | Ser | |
| | | | 500 | | | | 505 | | | | 510 | | | | | |
| atc | tat | ttg | cca | ggt | aac | gcg | aga | aat | att | aat | gtt | tac | gct | aaa | gaa | 1584 |
| Ile | Tyr | Leu | Pro | Gly | Asn | Ala | Arg | Asn | Ile | Asn | Val | Tyr | Ala | Lys | Glu | |
| | | 515 | | | | 520 | | | | 525 | | | | | | |
| tgc | act | ggt | tta | gct | tgg | gaa | tgg | tgg | aga | acg | gta | att | gat | gac | cgg | 1632 |
| Cys | Thr | Gly | Leu | Ala | Trp | Glu | Trp | Trp | Arg | Thr | Val | Ile | Asp | Asp | Arg | |
| | 530 | | | | 535 | | | | 540 | | | | | | | |
| aac | tta | cca | ctt | gtg | aaa | aat | aga | aat | atc | tcc | atc | tgg | ggc | acc | acg | 1680 |
| Asn | Leu | Pro | Leu | Val | Lys | Asn | Arg | Asn | Ile | Ser | Ile | Trp | Gly | Thr | Thr | |
| 545 | | | | 550 | | | | 555 | | | | 560 | | | | |
| ctt | tat | ccg | aaa | tat | agt | aat | aaa | gta | gat | aat | cca | atc | gaa | tat | gca | 1728 |
| Leu | Tyr | Pro | Lys | Tyr | Ser | Asn | Lys | Val | Asp | Asn | Pro | Ile | Glu | Tyr | Ala | |
| | | | 565 | | | | 570 | | | | 575 | | | | | |
| tta | gcc | tat | gga | agt | cag | ggt | gat | ctt | aat | cca | tta | att | aat | gaa | atc | 1776 |
| Leu | Ala | Tyr | Gly | Ser | Gln | Gly | Asp | Leu | Asn | Pro | Leu | Ile | Asn | Glu | Ile | |
| | | | 580 | | | | 585 | | | | 590 | | | | | |
| agc | aaa | atc | att | tca | gct | gca | gtt | ctt | tcc | tct | tta | aca | tcg | aag | cta | 1824 |
| Ser | Lys | Ile | Ile | Ser | Ala | Ala | Val | Leu | Ser | Ser | Leu | Thr | Ser | Lys | Leu | |
| | | 595 | | | | 600 | | | | 605 | | | | | | |
| cct | gca | gag | ttc | gtt | agg | cgc | gga | tcc | gga | att | cga | agc | tta | tcg | atg | 1872 |
| Pro | Ala | Glu | Phe | Val | Arg | Arg | Gly | Ser | Gly | Ile | Arg | Ser | Leu | Ser | Met | |
| | 610 | | | | 615 | | | | 620 | | | | | | | |
| tcg | acg | tag | | | | | | | | | | | | | | 1881 |
| Ser | Thr | | | | | | | | | | | | | | | |
| 625 | | | | | | | | | | | | | | | | |

<210> SEQ ID NO 2
<211> LENGTH: 626
<212> TYPE: PRT
<213> ORGANISM: Mycobacterium

<400> SEQUENCE: 2

-continued

```
Met Thr Asp Val Ser Arg Lys Ile Arg Ala Trp Gly Arg Arg Leu Met
1               5                   10                  15

Ile Gly Thr Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Ser Ala Lys Gln Ser Ala Ala Asn Lys Leu His Ser
    50                  55                  60

Ala Gly Gln Ser Thr Lys Asp Ala Ser Ala Phe Asn Lys Glu Asn Ser
65                  70                  75                  80

Ile Ser Ser Met Ala Pro Pro Ala Ser Pro Ala Ser Pro Lys Thr
                85                  90                  95

Pro Ile Glu Lys Lys His Ala Asp Glu Ile Asp Lys Tyr Ile Gln Gly
            100                 105                 110

Leu Asp Tyr Asn Lys Asn Asn Val Leu Val Tyr His Gly Asp Ala Val
        115                 120                 125

Thr Asn Val Pro Pro Arg Lys Gly Tyr Lys Asp Gly Asn Glu Tyr Ile
    130                 135                 140

Val Val Glu Lys Lys Lys Ser Ile Asn Gln Asn Asn Ala Asp Ile
145                 150                 155                 160

Gln Val Val Asn Ala Ile Ser Ser Leu Thr Tyr Pro Gly Ala Leu Val
                165                 170                 175

Lys Ala Asn Ser Glu Leu Val Glu Asn Gln Pro Asp Val Leu Pro Val
            180                 185                 190

Lys Arg Asp Ser Leu Thr Leu Ser Ile Asp Leu Pro Gly Met Thr Asn
        195                 200                 205

Gln Asp Asn Lys Ile Val Val Lys Asn Ala Thr Lys Ser Asn Val Asn
    210                 215                 220

Asn Ala Val Asn Thr Leu Val Glu Arg Trp Asn Glu Lys Tyr Ala Gln
225                 230                 235                 240

Ala Tyr Pro Asn Val Ser Ala Lys Ile Asp Tyr Asp Asp Glu Met Ala
                245                 250                 255

Tyr Ser Glu Ser Gln Leu Ile Ala Lys Phe Gly Thr Ala Phe Lys Ala
            260                 265                 270

Val Asn Asn Ser Leu Asn Val Asn Phe Gly Ala Ile Ser Glu Gly Lys
        275                 280                 285

Met Gln Glu Glu Val Ile Ser Phe Lys Gln Ile Tyr Tyr Asn Val Asn
    290                 295                 300

Val Asn Glu Pro Thr Arg Pro Ser Arg Phe Phe Gly Lys Ala Val Thr
305                 310                 315                 320

Lys Glu Gln Leu Gln Ala Leu Gly Val Asn Ala Glu Asn Pro Pro Ala
                325                 330                 335

Tyr Ile Ser Ser Val Ala Tyr Gly Arg Gln Val Tyr Leu Lys Leu Ser
            340                 345                 350

Thr Asn Ser His Ser Thr Lys Val Lys Ala Ala Phe Asp Ala Ala Val
        355                 360                 365

Ser Gly Lys Ser Val Ser Gly Asp Val Glu Leu Thr Asn Ile Ile Lys
    370                 375                 380

Asn Ser Ser Phe Lys Ala Val Ile Tyr Gly Gly Ser Ala Lys Asp Glu
385                 390                 395                 400

Val Gln Ile Ile Asp Gly Asn Leu Gly Asp Leu Arg Asp Ile Leu Lys
                405                 410                 415

Lys Gly Ala Thr Phe Asn Arg Glu Thr Pro Gly Val Pro Ile Ala Tyr
            420                 425                 430
```

```
Thr Thr Asn Phe Leu Lys Asp Asn Glu Leu Ala Val Ile Lys Asn Asn
        435                 440                 445

Ser Glu Tyr Ile Glu Thr Thr Ser Lys Ala Tyr Thr Asp Gly Lys Ile
    450                 455                 460

Asn Ile Asp His Ser Gly Gly Tyr Val Ala Gln Phe Asn Ile Ser Trp
465                 470                 475                 480

Asp Glu Val Asn Tyr Asp Pro Glu Gly Asn Glu Ile Val Gln His Lys
                485                 490                 495

Asn Trp Ser Glu Asn Asn Lys Ser Lys Leu Ala His Phe Thr Ser Ser
                500                 505                 510

Ile Tyr Leu Pro Gly Asn Ala Arg Asn Ile Asn Val Tyr Ala Lys Glu
        515                 520                 525

Cys Thr Gly Leu Ala Trp Glu Trp Trp Arg Thr Val Ile Asp Asp Arg
        530                 535                 540

Asn Leu Pro Leu Val Lys Asn Arg Asn Ile Ser Ile Trp Gly Thr Thr
545                 550                 555                 560

Leu Tyr Pro Lys Tyr Ser Asn Lys Val Asp Asn Pro Ile Glu Tyr Ala
                565                 570                 575

Leu Ala Tyr Gly Ser Gln Gly Asp Leu Asn Pro Leu Ile Asn Glu Ile
                580                 585                 590

Ser Lys Ile Ile Ser Ala Ala Val Leu Ser Ser Leu Thr Ser Lys Leu
        595                 600                 605

Pro Ala Glu Phe Val Arg Arg Gly Ser Gly Ile Arg Ser Leu Ser Met
        610                 615                 620

Ser Thr
625
```